United States Patent [19]

Magrath et al.

[11] Patent Number: 5,582,973
[45] Date of Patent: Dec. 10, 1996

[54] SENSITIVE METHOD FOR LOCALIZING CHROMOSOMAL BREAKPOINTS

[75] Inventors: Ian T. Magrath, Silver Spring, Md.; Bruce Shiramizu, Pacifica, Calif.

[73] Assignee: The United States of America as represented by the Department of Health and Human Services, Washington, D.C.

[21] Appl. No.: 160,547

[22] Filed: Dec. 2, 1993

Related U.S. Application Data

[63] Continuation of Ser. No. 698,233, May 6, 1991, abandoned, which is a continuation of Ser. No. 441,516, Nov. 24, 1989, abandoned.

[51] Int. Cl.⁶ .............................. C12Q 1/68; C12P 19/34; C07H 21/04
[52] U.S. Cl. .......................... 435/6; 435/91.2; 536/24.31; 536/24.33
[58] Field of Search .................. 435/6, 91.2; 536/24.33, 536/24.31; 935/77, 78

[56] References Cited

U.S. PATENT DOCUMENTS

| | | | |
|---|---|---|---|
| 4,683,195 | 7/1987 | Mullis et al. | 435/6 |
| 4,701,409 | 10/1987 | Croce | 435/6 |

*Primary Examiner*—George C. Elliott
*Attorney, Agent, or Firm*—Townsend and Townsend and Crew LLP

[57] ABSTRACT

A sensitive method for identifying chromosomal breakpoints flanked by repeat sequences, through amplification by polymerase chain reaction, is described. The application of the method to the detection of Burkitt's lymphoma cells is demonstrated.

20 Claims, 4 Drawing Sheets

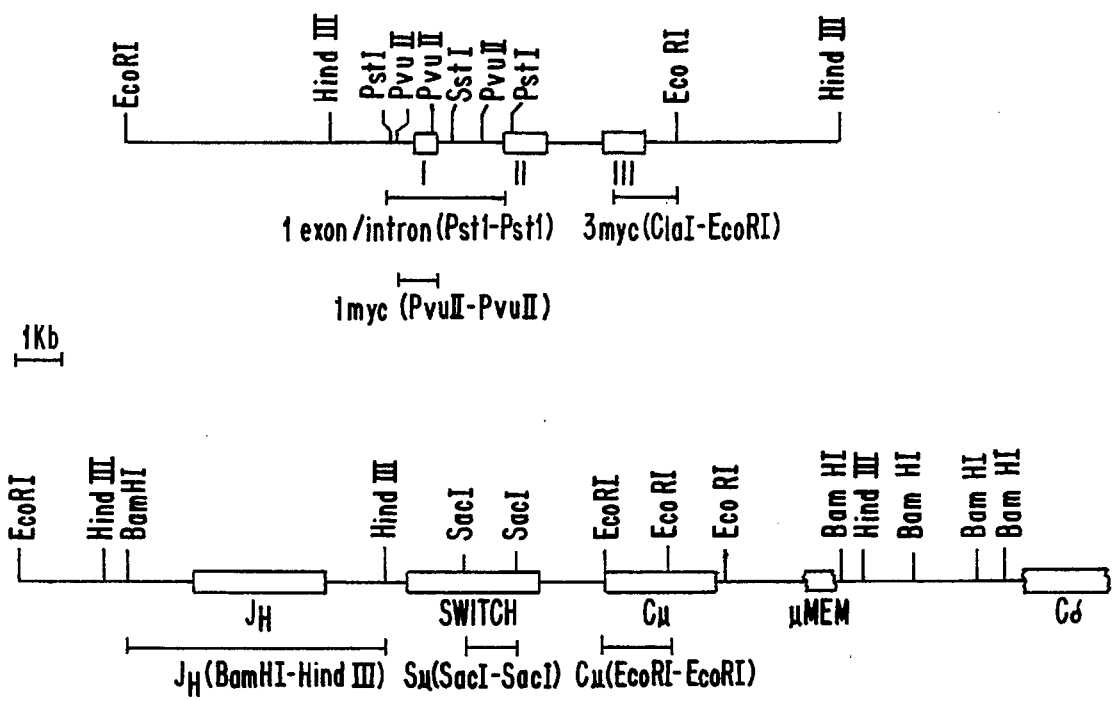
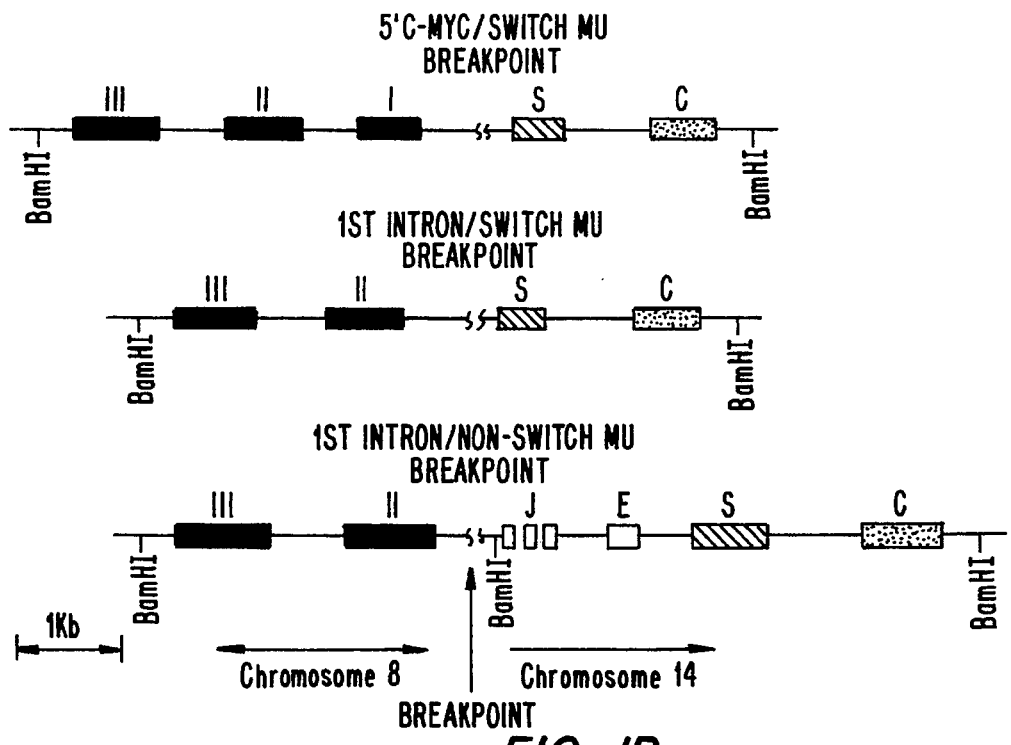
FIG. 1A.
FIG. 1B.

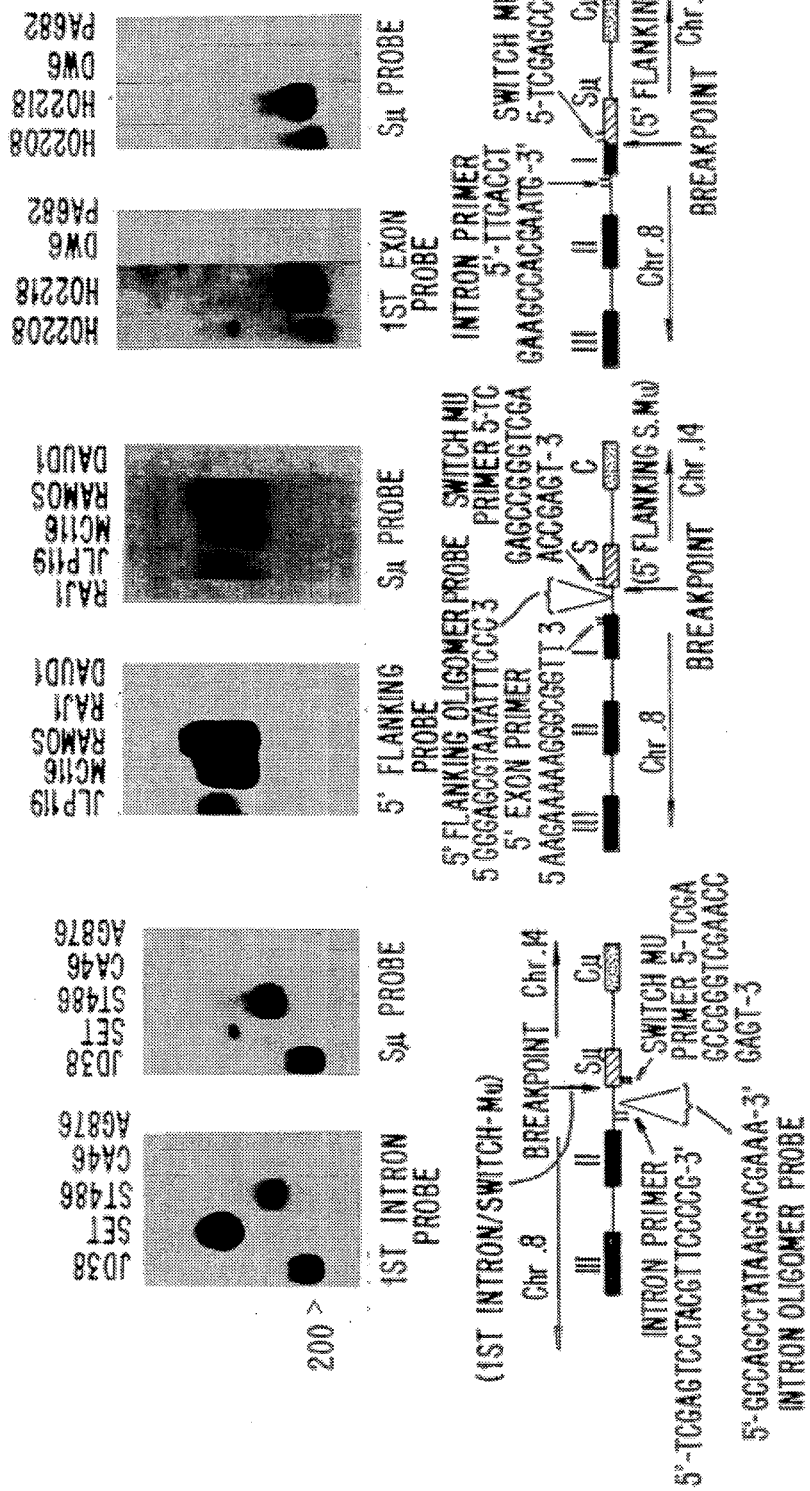

SENSITIVE METHOD FOR LOCALIZING CHROMOSOMAL BREAKPOINTS

This is a continuation of application Ser. No. 07/698,233 now abandoned filed May 6, 1991, which is a continuation of application Ser. No. 07/441,516, filed Nov. 24, 1989 (abandoned).

The present invention is related generally to the techniques for localizing chromosomal breakpoints associated with chromosomal translocations. More particularly, the present invention is related to a sensitive method for identifying chromosomal breakpoints which are flanked by repeat regions through amplification by polymerase chain reaction. An application of the method to the detection of Burkitt's lymphoma is demonstrated.

BACKGROUND OF THE INVENTION

Present techniques to detect chromosomal breakpoint locations at a molecular level utilize Southern blotting or direct sequencing and cloning of DNA. A limitation of Southern blotting is that it requires a greater amount of tumor sample in order to analyze the DNA and multiple digestions with restriction endonucleases are necessary. Moreover, the results from the tests need to be compared with control samples, a process which is subjective and can, on occasion, lead to error.

Other techniques, such as direct sequencing and cloning of the DNA are cumbersome and time consuming. Cytogenetic analysis does not provide identification of the breakpoint locations at a molecular level and is relatively insensitive. Flow cytometry requires a larger number of cells for analysis and suffers from the disadvantage that with the exception of anti-idiotype markers, no truly tumor specific marker detectable by this technique exists. Until now, the most precise means of identifying breakpoint locations has been molecular cloning, but this method is too cumbersome for routine clinical use or for the analysis of a large number of tumors. Southern blotting is more practical. However, for the reasons stated above, Southern blotting does not provide much greater sensitivity than microscopy.

SUMMARY OF THE INVENTION

It is, therefore, an object of the present invention to provide a sensitive and efficient method for localizing chromosomal breakpoints by amplifying a fragment containing the breakpoint, making use of repeat sequences flanking one side of the breakpoint by the polymerase chain reaction (PCR). The use of repeat sequences present on one chromosome markedly reduces the number of "trials" with different oligimer pairs that would be needed to find a pair which results in the amplification of the breakpoint-containing fragment. Repeat sequences of various kinds occur scattered throughout the genome and any of these may be used in this approach. In Burkitt's lymphoma, the breakpoint on chromosome 14 is often within a region containing many repeat sequences known as a "heavy chain switch region", and it was, therefore chosen to use tumors with breakpoints in this region to demonstrate the feasibility of the approach.

It is another object of the present invention to provide a diagnostic tumor marker for Burkitt's lymphoma with 8;14 translocations, and a new method of simultaneously subdividing Burkitt's lymphoma into subtypes based on the location of chromosomal breakpoints.

Various other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIGS. 1a and 1b schematically illustrate restriction map and breakpoint locations using Burkitt's lymphoma as an example. (a) Restriction map of the c-myc locus on chromosome 8 and Ig heavy chain locus on chromosome 14; and (b) the structures of the translocated c-myc gene locus for three of several possible breakpoint regions. Here depicted are translocations occurring 5' of the c-myc region and in the $S\mu$ region (upper); 1st c-myc intron and $S\mu$ region (middle) and 1st c-myc intron and non-$S\mu$ regions (bottom) for t(8;14) cells.

FIGS. 3A–3C show the results of hybridization of PCR products. Primer pairs, appropriate probes, and a diagram of the structure of the translocated regions are shown. (A) 1st intron breakpoint: primers for 1st intron/$S\mu$ regions were used as shown in the lower diagrammatic part of the figure. Above, amplification products hybridized with intron and $S\mu$ probes. CA46 and AG876 are control cell lines. (B) 5' flanking sequences/$S\mu$ breakpoint: primers for $S\mu$ and the 5' end of 1st exon as shown, were used. Amplification products were hybridized with 5' flanking and $S\mu$ probes. RAJI and DAUDI are control cell lines. (C) 1st exon breakpoint: primers for $S\mu$ and 5' and of the 1st intron as shown were used. Amplification products were hybridized with 1st exon and $S\mu$ probes. DW6 and PA682 are control cell lines.

DETAILED DESCRIPTION OF THE INVENTION

Figure 2A:
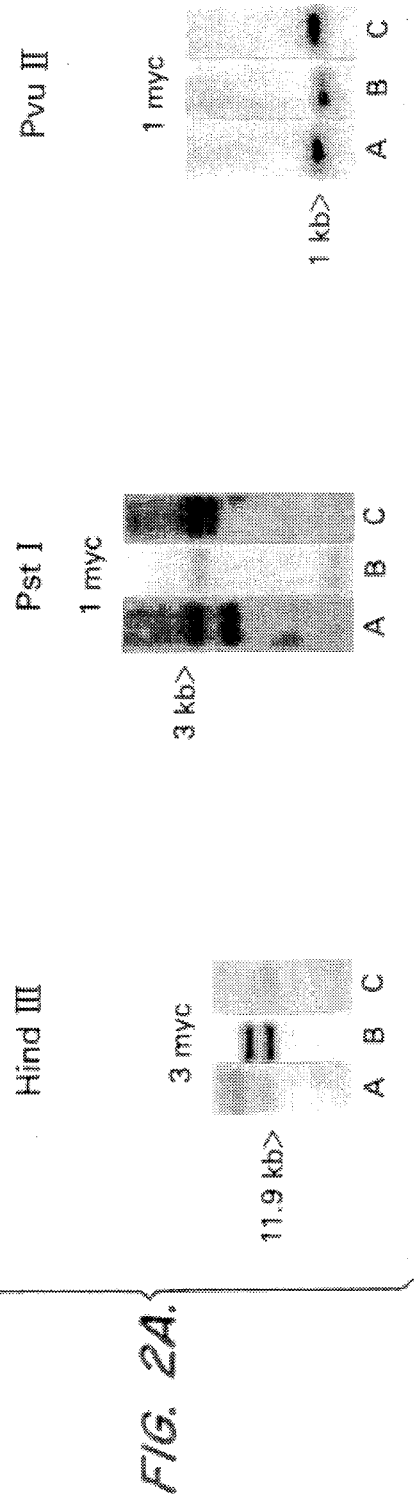
FIGS. 2A and 2B present Southern data used to corroborate the PCR data. Example of Southern blotting are shown for tumors/cell lines designated as ST486, SET, and DW6 (A,B and C respectively) demonstrating intron breakpoint. ST486 and SET have breakpoints on chromosome 14 in the $S\mu$ region. DW6 has a breakpoint outside the $S\mu$ region.

The above and various other objects and advantages of the present invention are achieved by a method for localizing chromosomal breakpoints, comprising the steps of (a) preparing several pairs of oligomers, one member of which contains a primer that specifically hybridizes with repetitive sequences in the DNA flanking the breakpoint and the second member containing a primer that hybridizes to some part of a gene involved in the translocation, situated on the other side of the breakpoint; (b) then amplifying the DNA by PCR; and (c) determining the presence of breakpoints by demonstrating an amplified band with one of the oligomer pairs and, if desired, prove the presence of sequences from two chromosomes by Southern blot analysis and hybridization with 32P labeled or other suitably labeled probes.

Unless defined otherwise, all technical and scientific terms used herein have the same meaning as commonly understood by one of ordinary skill in the art to which this invention belongs. Although any methods and materials similar or equivalent to those described herein an be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

MATERIALS AND METHODS

Samples and DNA preparation. The majority of the cell lines and tumor samples were obtained from the tumors of patients treated in the NCI Pediatric Branch (see Table 1). Description of the derivation and characteristics of the cell lines can be found in Magrath et al (1980, *J. Natl. Cancer Inst*, 64:465) and Benjamin et al (1983, *Blood* 61:1017). DNA from these cell lines and tumors was extracted as described by Barriga et al (1988, *Blood* 72:792).

Restriction endonuclease digestion and Southern blotting. 20 μg of DNA was digested with restriction endonucleases: HindIII, PstI, PvuII, and BamHI using protocols provided by the supplier (Bethesda Research Laboratories, Bethesda, Md.). Southern blots were prepared, hybridized, and washed by standard procedures such as described in Barriga et al, supra, and Maniatis et al (1982, Molecular Cloning: A Laboratory Manual, Cold Spring Harbor, Cold Spring Harbor Laboratory Press). The following probes were used to determine the breakpoint locations on chromosomes 8 and 14: Cμ (EcoRI-RcoRI) (Ravetch et al, 1982, *Proc. Natl. Acad. Sci. USA* 79:6497); 3rd exon c-myc (ClaI-EcoRI) (Dalla-Favera et al, 1982, *Proc. Natl. Acad. Sci. USA* 79:6497); 1st exon c-myc (PvuII-PvuII) (Dalla-Favera et al, 1983, *Science* 219:953); $J_k$ (BamHI-HindIII) (Ravetch et al. supra); Sμ (SacI-SacI) (Ravetch et al, supra). The probes were labeled with $^{32}P$ (New England Nuclear Dupont, Wilmington, Del.) using a nick-translation kit (Bethesda Research Laboratories, Bethesda, Md.).

Polymerase chain reaction. Oligonucleotide primers and probes, based on published sequence information, were synthesized by synthecell (Rockville, Md.) and on an Applied Biosystems (Foster City, Calif.) DNA synthesizer (Gelmann et al, 1983, *Nature* 306:700: Bernard et al, 1983, *EMBO J* 2:2375; Petrini et al, 1987, *J. Immunology* 138:1940). 200 ng of each tumor cell DNA was subjected to PCR essentially as described by Saiki et al (1988, *Science* 239:487). Amplification with Taq (*Thermus aquatious*) polymerase took place in 100 μl reaction mixtures containing the DNA in 50 mM KCl, 10 mM Tris-HCl (pH 8.3 at room temperature), 1.5 mM $MgCl_2$, 0.01% gelatin (w/v), each primer at 1 μM, each dNTP (dATP, dCTP, TTP, dGTP) at 200 μm. The samples were heated to 95° C. for 2 minutes, cooled to room temperature (about 22°–24° C.) prior to adding 2 units of polymerase and subjected to 25–30 cycles of PCR. An aliquot of the PCR reaction was processed and transferred to a nylon membrane, hybridized to appropriate probes and autoradiographed by standard techniques such as described by Maniatis et al, supra.

Sensitivity tests. DNA was extracted from cell suspensions containing various proportions of ST486 and DAUDI cells from a dilution of $1:10^6$ cells to $1:10^6$ cells. Subsequently, the DNA was subjected to PCR and an aliquot of the reaction product processed as described above.

RESULTS

Figure 2B:
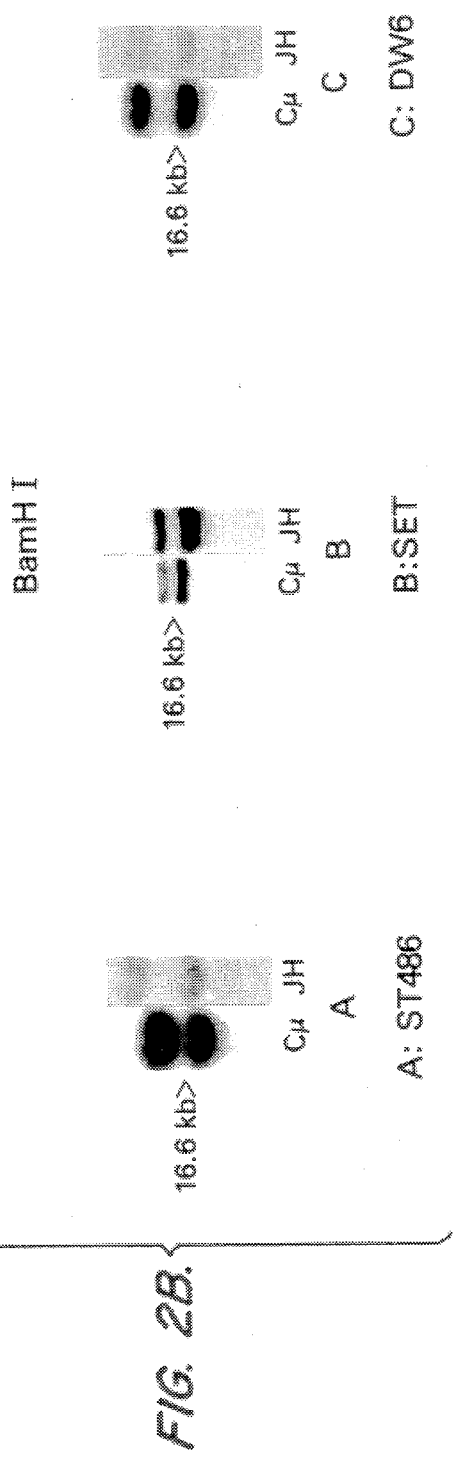

Southern blot analysis. This test was used to confirm the location of breakpoints. Restriction maps of the c-myc and Ig heavy chain loci and examples of the possible 8;14 translocation products are shown in FIG. 1. An example of autoradiographs of Southern blots obtained with various restrictions enzyme/DNA probe combinations are shown in FIG. 2.

The breakpoint locations, as detected by Southern blotting, are summarized in Table 1. The breakpoints in ST486. CA46 and RAJI have been previously cloned and sequenced (Galmann et al. supra; Nishikura et al, 1985, *Proc. Natl. Acad. Sci. USA* 82:2900; Showe et al, 1985. *Molecular and Cellular Biology* 5:501). In both RAJI and MC116, c-myc transcripts contain a 1st exon, and S1 protection analysis confirms initiation from at least one of the major c-myc promoters, $P_1$ and $P_2$ (Barriga et al, 1988, *Current Topics in Microbiology and Immunology* 141:125; Nishikura et al, supra)

1st nitron breakpoints. Using the primers for Sμ and 1st intron c-myc regions, it became possible to amplify a fragment in three tumors: ST486, JD36, and SET (FIG. 3A). In each case the amplified fragments hybridized with both Sμ and 1st intron c-myc probes. To further confirm the amplification of the targeted sequences, oligomer probes encompassing part of the DNA that is expected to be amplified were labeled and hybridized to the same samples. The results obtained were quite similar (data not shown). The ability of this primer pair to specifically amplify fragments from tumors containing switch/intron breakpoints was substantiated by showing that under the conditions used, amplified fragments were not obtained in PCR performed in 12 additional tumors containing chromosomal breakpoints in different regions of c-myc including first exon and 5' flanking regions. Of note is the failure to amplify fragments in RAJI and CA46, which also have first intron breakpoints, but involve $S\gamma_1$ and $S\alpha_1$, respectively, rather than Sμ (FIG. 3A). Thus the switch oligomer proved to be quite specific to Sμ sequences and permits differentiation between breakpoints in different switch regions in the heavy chain locus.

Immediate 5' and 1st exon c-myc 5' breakpoints. When primers derived from Sμ and a region at the 5' end of the 1st exon of c-myc were used, amplification of a DNA fragment was observed in MC116, JLP119, and RAMOS (FIG. 3B). Similarly, using a primer from the 5' end of the 1st intron of c-myc, it was possible to identify fragments from DNA obtained from two tumor biopsies in which the chromosome 8 breakpoint is within the 1st exon of c-myc (FIG. 3C). In each case, the amplified fragments were shown to contain sequences from both chromosomes 8 and 14 by hybridization with specific probes (FIG. 3). Moreover, the primer pairs failed to amplify fragments from tumors with breakpoint in different regions of chromosome 8 (e.g. the 5' flanking sequences).

Figure 4:
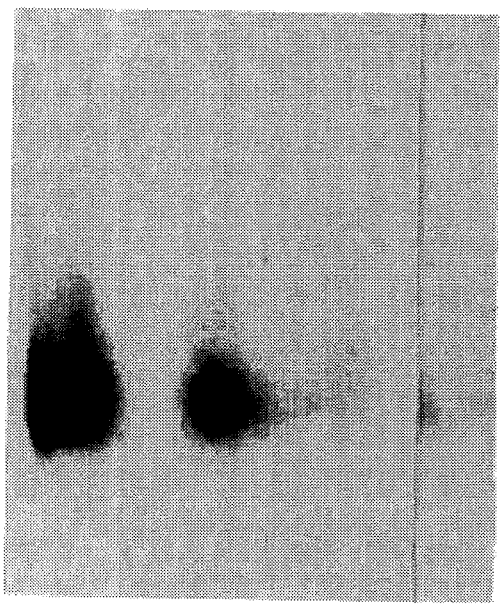
FIG. 4 demonstrates the sensitivity of the method of the present invention. DNA extracted from cell suspensions containing various proportions of ST466 and DAUDI cells as indicated. Hybridized with $S\mu$ probe.

Sensitivity of PCR. The presence of a chromosomal translocation provides a tumor specific marker. DNA was extracted from cell suspensions of ST486 and DAUDI cells containing as few as 1 cell of ST480 per $10^6$ DAUDI cells and was subjected to 30–50 cycles of PCR. Results using the Sμ probe are shown in FIG. 4 which demonstrates the extreme sensitivity of the technique of the present invention. The technique enables the detection of as few as 1 neoplastic cell in about $10^6$ cells which makes it possible to detect minimal residue) disease following treatment, or small quantities of tumor cells mixed with normal cells before treatment.

In summary, the results indicate that the use of different oligomer pairs permits not only the detection of 8;14 translocations, but also the localization of breakpoints to specific regions of the c-myc gene. Unique to this method is the incorporation of repeat sequences in one of the amplification oligomers. As mentioned above, the second oligomer is derived from the gene involved in the translocation. Clearly, the present invention now allows the diagnosis and the detection of the quantities of cells bearing specific translocations in various organs or tissues of the body before, during or after treatment.

It us understood that the examples and embodiments described herein are for illustrative purposes only and that various modifications or changes in light thereof will be suggested to persons skilled in the art and are to be included within the spirit and purview of this application and scope of the appended claims.

TABLE 1

Summary of Breakpoint Locations of Samples Subjected to PCR

| Sample | Translocation | Chr.8 Breakpoint* | Chr.14 Breakpoint |
|---|---|---|---|
| JD38 | 8;14 | 1st Intron | $S\mu^{\alpha}$ |
| BET | 8;14 | 1st Intron | $S\mu$ |
| ST486 | 8;14 | 1st Intron | $S\mu$ |
| JLP119 | 8;14 | Immed. 5' | $S\mu$ |
| MC116 | 8;14 | Immed. 5' | $S\mu$ |
| RAMOS | 8;14 | Immed. 5' | $S\mu$ |
| HO2208 | 8;14 | 1st Exon | $S\mu$ |
| HO2218 | 8;14 | 1st Exon | $S\mu$ |
| CA46 | 8;14 | 1st Intron | $S\alpha^{\delta}$ |
| RAJI | 8;14 | Immed. 5' | $S\tau^{\#}$ |
| AG876 | 8;14 | Far 5' | $J_H^{\P}$ |
| DAUDI | 8;14 | Far 5' | $D_H^{**}$ |
| DW6 | 8;14 | 1st Intron | $J_H$ |
| EW36 | 8;14 | Far 5' | $NS\mu\text{-}NJ_H^{\alpha\alpha}$ |
| P3HR1 | 8;14 | Far 5' | $NS\mu$ |
| PA682 | 8;22 | 3' | Lambda-$V^{\S\S}$ |
| KK124 | 8;22 | 3' | Lambda-$C^{\#\#}$ |
| MOLT | None | None | None |

*Location with respect to c-myc
$^{\alpha}$Switch-mu loci
$^{\delta}$Switch-alpha loci
$^{\#}$Switch-gamma loci
$^{\P}$J-Heavy loci
**D-Heavy
$^{\alpha\alpha}$Non-S$\mu$;Non-J$_H$
$^{\S\S}$Lambda-Variable loci
$^{\#\#}$Lambda-Constant loci

What is claimed is:

1. A method for localizing breakpoints between human chromosome 8 and chromosomes 14 or 22 when involved in a translocation between the chromosomes using a polymerase chain reaction, the method comprising the steps of:
   (a) preparing a PCR mixture having:
      (i) a segment of nucleic acid having a portion of chromosome 8 and a portion of chromosome 14 or 22 and
      (ii) a PCR primer pair of at least two members in which a first member binds to a portion of the c-myc gene of chromosome 8 and the second member binds to a repeat region within a gene encoding an immunoglobin chain on chromosome 14 or 22;
   (b) conducting a PCR amplification of the segment of nucleic acid; and,
   (c) identifying the presence of the amplified segment of step (b) using a labeled probe,
thereby localizing said breakpoint between human chromosome 8 and chromosomes 14 or 22.

2. A method of claim 1 wherein the first member of the PCR primer pair binds to the first intron of c-myc.

3. A method of claim 1 wherein the first member of the primer pair binds to the first exon of c-myc.

4. A method of claim 1 wherein the second member of the primer pair binds to a repeat region within a member of the group consisting of a heavy chain region of chromosome 14, a Lambda-variable loci of chromosome 22 and a Lambda-constant loci of chromosome 22.

5. A method of claim 4 wherein the second member of the primer pair binds to a repeat region within a heavy chain switch region of chromosome 14.

6. A method of claim 5 wherein the second member of the primer pair binds to a repeat region in the Switch-mu loci.

7. A method of claim 5 wherein the second member of the primer pair binds to a repeat region in the Switch-alpha loci.

8. A method of claim 5 wherein the second member of the primer pair binds to a repeat region in the Switch-gamma loci.

9. A method of claim 4 wherein the second member of the primer pair binds to a repeat region in a J-Heavy loci.

10. A method of claim 3 wherein the second member of the primer pair binds to a repeat region in Switch-mu region of chromosome 14.

11. A PCR reaction mixture for localizing breakpoints in between human chromosome 8 and chromosomes 14 and 22 when involved in a translocation between the chromosomes the mixture comprising a PCR primer pair of at least two members in which the first member binds to a portion of the c-myc gene of chromosome 8 and the second member binds to a repeat region within a gene encoding an immunoglobin chain on chromosome 14 or 22.

12. A mixture of claim 11 wherein the first member of the primer pair binds to the first intron of c-myc.

13. A mixture of claim 11 wherein the first member of the primer pair binds to the first exon of c-myc.

14. A mixture of claim 11 wherein the second member binds to a member of the group consisting of a heavy chain region of chromosome 14, a Lambda-variable loci of chromosome 22 and a Lambda-constant loci of chromosome 22.

15. A mixture of claim 11 wherein the second member of the primer pair binds to a repeat region within a heavy chain switch region of chromosome 14.

16. A mixture of claim 15 wherein the second member of the primer pair binds to a repeat region in the Switch-mu loci.

17. A mixture of claim 15 wherein the second member of the primer pair binds to a repeat region in the Switch-alpha loci.

18. A mixture of claim 15 wherein the second member of the primer pair binds to a repeat region in the Switch-gamma loci.

19. A mixture of claim 14 wherein the second member of the primer pair binds to a repeat region in a J-Heavy loci.

20. A mixture of claim 13 wherein the second member of the primer pair binds to a repeat region in Switch-mu region of chromosome 14.

* * * * *